United States Patent [19]

Vogel et al.

[11] Patent Number: 5,356,460
[45] Date of Patent: Oct. 18, 1994

[54] REMOVAL OF METHACROLEIN FROM A GASEOUS MIXTURE

[75] Inventors: Herbert Vogel, Ludwigshafen; Herbert Exner, Waldsee; Gerd Bohner, Bad Schoenborn, all of Fed. Rep. of Germany

[73] Assignee: BASF Aktiengesellschaft, Ludwigshafen, Fed. Rep. of Germany

[21] Appl. No.: 95,986

[22] Filed: Jul. 23, 1993

[30] Foreign Application Priority Data

Jul. 31, 1992 [DE] Fed. Rep. of Germany ....... 4225321

[51] Int. Cl.$^5$ .................. C07C 47/22; B01D 53/14
[52] U.S. Cl. ........................... 95/237; 95/240; 423/245.2
[58] Field of Search ............... 423/245.2; 95/240, 237

[56] References Cited

U.S. PATENT DOCUMENTS

| | | | |
|---|---|---|---|
| 4,234,519 | 11/1980 | Yeoman et al. | 568/492 |
| 4,618,709 | 10/1986 | Sada et al. | 568/492 |
| 5,248,819 | 9/1993 | Matsumoto et al. | 562/532 |

FOREIGN PATENT DOCUMENTS

| | | | |
|---|---|---|---|
| 2842092 | 4/1979 | Fed. Rep. of Germany | 95/237 |
| 2004886 | 4/1979 | United Kingdom . | |

OTHER PUBLICATIONS

Chemical Abstracts, vol. 112, No. 12, Mar. 19, 1990, AN-99474y, M. Kuragano, et al., "Absorption of Methacrolein by Aqueous Methacrylic Acid".

*Primary Examiner*—Wayne Langel
*Assistant Examiner*—Peter T. DiMauro
*Attorney, Agent, or Firm*—Oblon, Spivak, McClelland, Maier & Neustadt

[57] ABSTRACT

Methacrolein is removed from a gaseous mixture by absorption by means of an aqueous solution which contains from 60 to 90% by weight of methacrylic acid.

3 Claims, No Drawings

REMOVAL OF METHACROLEIN FROM A GASEOUS MIXTURE

The present invention relates to a process for removing methacrolein from a gaseous mixture by absorption by means of an aqueous solution containing methacrylic acid.

Methacrolein can be produced, inter alia, by catalytic gas-phase oxidation of $C_4$ compounds such as butane, isobutene, tert-butanol or isobutyraldehyde (cf., for example, DE-A 28 42 092). However, this process does not give pure methacrolein but gives a gaseous mixture from which the methacrolein must, as a rule, be removed for the preparation of subsequent products. However, even when the gas mixture produced in the catalytic gas-phase oxidation can be employed directly for preparing the subsequent products, there is often the problem of removing unreacted methacrolein from the gas mixture containing the subsequent product. This applies in particular to the conversion of methacrolein into methacrylic acid which is, just like the preparation of methacrolein itself, advantageously carried out by catalytic gas-phase oxidation. However, the reaction conditions with which the selectivity of methacrylic acid formation is high are, with most of the currently available catalysts, associated with a relatively low methacrolein conversion, which is why removal of unreacted methacrolein from the gaseous reaction mixture and return thereof to the oxidation reactor represents an essential factor especially with respect to the economics of the overall process.

DE-A 28 42 092 discloses the initial absorption of the methacrolein from such gaseous mixtures using a liquid absorbent, and the isolation of the methacrolein from the resulting methacrolein-containing solution by distillation or by stripping. The recommended absorbent is an aqueous solution containing methacrylic acid in an amount of at least 5% by weight.

The advantage of using an aqueous methacrylic acid solution as absorbent is, inter alia, that methacrylic acid and methacrolein are related species and, as a rule, the former essentially does not interfere with subsequent reactions of methacrolein, which is usually, after the removal, associated with traces of the absorbent used.

Furthermore, U.S. Pat. No. 4,618,709 discloses that the absorption coefficient of an aqueous solution containing methacrylic acid for methacrolein increases with the content of methacrylic acid. However, methacrylic acid is an $\alpha,\beta$-monoethylenically unsaturated compound and, as such, displays a pronounced tendency to polymerization which, in solution, normally increases with the concentration. Although it is possible to counter this by adding an increased amount of polymerization inhibitors, it is generally undesirable for large amounts of foreign substance to be present. This is why the aqueous solutions containing methacrylic acid which are used in the prior art for absorbing methacrolein always have methacrylic acid contents $\leq 45\%$ by weight (DE-A 28 42 092 and U.S. Pat. No. 4,618,709).

The disadvantage of these prior art methods is, however, that the absorption coefficient for methacrolein is unsatisfactory, and attempts have been made in the prior art to counter this by a) carrying out the absorption at low temperatures and/or using increased amounts of absorbent (DE-A 28 42 092) or b) adding acetic acid, which is recommended as agent to increase the absorption coefficient for methacrolein (U.S. Pat. No. 4,618,709).

However, the disadvantage of these remedies is that dilute aqueous methacrylic acid solutions containing methacrolein undergo phase separation at low temperatures, and one of the two phases contains methacrolein at high concentration. The latter is a disadvantage because the tendency of methacrolein to polymerize increases with its concentration.

The presence of acetic acid is disadvantageous since it means the introduction of another foreign substance.

It is an object of the present invention to provide a process for absorbing methacrolein from a gaseous mixture which does not have the said disadvantages.

We have found that this object is achieved by a process for removing methacrolein from a gaseous mixture by absorption by means of an aqueous solution containing methacrylic acid, wherein the methacrylic acid content of the aqueous solution is form 60 to 90% of its total weight.

The basis for the process according to the invention is the finding that the tendency of an aqueous methacrylic acid solution to polymerize is, surprisingly, considerably less when the methacrylic acid content is $\geq 60\%$ by weight that when it is in the region of 40% by weight.

Another noteworthy property of aqueous solutions containing from 60 to 90% by weight of methacrylic acid compared with corresponding solutions with a lower methacrylic acid content is that their tendency to phase separation on absorption of methacrolein even at low temperatures is very much less pronounced or that such a phase separation in fact does not occur at all. The latter is true, for example, of a 60% by weight aqueous methacrylic acid solution at 20° C. and under 1 atm, but not of a $\leq 50\%$ by weight aqueous methacrylic acid solution under the same conditions.

The process according to the invention is thus advantageous compared with prior art processes in that the absorbent has a higher absorption coefficient for methacrolein at a given absorption temperature and, at the same time, absorption can be carried out without phase separation at lower temperature, which results in a further increase in the absorption coefficient.

The absorption process according to the invention is advantageously carried out in such a way that the temperature in the absorption apparatus is from 5° to 50°, preferably from 20° to 40°, and very particularly preferably from 30° to 35° C., which reduces the use of elaborate cooling equipment and the associated energy consumption. The methacrolein can be removed from the resulting absorption solution by, for example, distillation and/or stripping.

With regard to the removal of the methacrolein by distillation, it is particularly advantageous that the boiling point of aqueous methacrylic acid solutions under atmospheric pressure is virtually independent of the methacrylic acid content over a wide concentration range (compare Zh. Prikl. Khim. 47 (1974) 2130) and increases markedly only above 85% by weight. The boiling point under 760 Torr is essentially 100° C. in the range from 30 to 85% by weight. The process according to the invention is therefore preferably carried out in the presence of an aqueous solution with a methacrylic acid content of from 60 to 80, particularly preferably 60 to 70, % by weight. The aqueous methacrylic acid solution remaining after removal of the methacrolein can be used for further absorptions.

The presence of additional carboxylic acids, e.g. acetic acid, in the absorbent does not, as a rule, interfere. Thus, the presence of small amounts of acetic acid for example results in an additional reduction in the tendency to phase separation. However, the content of acetic acid should not exceed 20, preferably 5, % of the weight of the aqueous solution used to absorb the methacrolein.

The methacrolein-containing gas mixture is otherwise scrubbed in a conventional way, for example in one absorption device or a plurality of devices arranged in series, but one device generally suffices. Counter current absorption is preferred, although parallel flow contact can be used, but this is less expedient. The zone in which contact between the gaseous mixture and the absorbent takes place can have a conventional design suitable for contact between a gas and a liquid. The type of absorption device used for this is not subject to any restriction. For example, it is possible to employ any conventional absorption towers such as packed, perforated plate, bubble cap or spray towers. It is expedient for the mixture which is to be washed to be under elevated pressure so that it easily flows through the scrubbing zones. The upper limit of the pressure is primarily determined by economic considerations. A gage pressure of $>0$ to $10^5$ Pa is normally expedient, and it is preferably $2 \times 10^4$ Pa. The amount of aqueous solution containing methacrylic acid which is to be used for the methacrolein absorption depends, inter alia, on the methacrolein content of the gas mixture to be washed. It can easily be established by the skilled worker in a few experiments.

The process according to the invention is particularly advantageous for removing methacrolein from gas mixtures which are obtained from the catalytic gas-phase oxidation of $C_4$ compounds to methacrolein. It is furthermore particularly advantageous for removing unreacted methacrolein from gas mixtures which are obtained from the catalytic gas-phase oxidation of methacrolein, or from catalytic gas-phase oxidation of $C_4$ compounds via methacrolein as intermediate to methacrylic acid.

In processes of this type, compounds such as butane, isobutene, tert-butanol or isobutyraldehyde are typically oxidized in a fixed bed tube bundle reactor in the presence of a multimetal oxide catalyst at from 250° to 550° C. with oxygen to methacrolein or in two consecutive stages (which can be spatially separate or combined) to methacrylic acid. In these exothermic reactions, the reactive gas components are normally reacted in the presence of large amounts of diluent gases to improve control of the reaction and dissipation of heat. Suitable diluent gases are inert gases such as nitrogen and carbon dioxide, as well as steam.

The gaseous reaction product therefore contains not only methacrolein and, where appropriate, methacrylic acid but also, in particular, large amounts of diluent gases, unreacted starting compounds and small amounts of organic by-products such as aldehydes, ketones or aliphatic carboxylic acids (e.g. acetic acid). The methacrolein content is usually below 5% by volume. In order to increase the methacrolein concentration before application of the process according to the invention, the reaction mixture is preferably subjected to one or more condensation steps. It is possible in this way to remove the constituents which have a higher boiling point than methacrolein. The gas mixture resulting from this is then subjected to the process according to the invention in a suitable absorption device.

It is subsequently possible for the methacrolein to be removed from the resulting absorption solution, e.g. by stripping with an inert gas, and to be returned together with the inert gas directly to the catalytic gas-phase oxidation or obtained pure by fractional distillation and used as such in a wide variety of subsequent reactions. It is also self-evident that the process steps according to the invention are carried out in the presence of effective amounts of polymerization inhibitors such as hydroquinone, hydroquinone monomethyl ether or phenothiazine. The amounts used normally range from 50 to 1000 ppm based on the $\alpha,\beta$-monoethylenically unsaturated compounds.

EXAMPLES

Example 1

Investigation of the tendency of solutions with different methacrylic acid contents to polymerize.

The aqueous methacrylic acid solutions (prepared by mixing appropriate amounts of water and methacrylic acid containing $\leq 0.1\%$ by weight of organic impurities) were refluxed and their viscosity was assessed visually as a function of time. They all contained 170 ppm, based on the amount of methacrylic acid present, of hydroquinone monomethyl ether as polymerization inhibitor.

Results:
a) 75% by weight aqueous methacrylic acid solution
   Boiling point: 98° C. No essential change in the viscosity detectable after six days.
b) 60% by weight aqueous methacrylic acid solution
   Boiling point: 98° C. Incipient change in viscosity detectable after four days.
c) 40% by weight aqueous methacrylic acid solution
   Boiling point: 98° C. Distinct increase in viscosity observed after only two days.

Example 2

Absorption according to the invention of methacrolein from a gas mixture (using hydroquinone as inhibitor).

tert-Butanol was oxidized by catalytic gas-phase oxidation to methacrolein with atmospheric oxygen in a fixed bed reactor in the presence of steam as further diluent gas. The product mixture at 250° C. contained 2.5% by volume methacrolein, 0.4% by volume methacrylic acid and by-products such as small amounts of acetic acid, as well as the diluent gases.

Higher-boiling components were condensed out in several steps, the last of which was carried out at 30° C.

The remaining gas mixture, which had a methacrolein content of 2.9% by volume, was fed at a rate of 2 m³/h to a countercurrent absorption column which was operated with a 60% by weight aqueous methacrylic acid solution as absorbent at about 30° C.

The resulting absorption solution contained 5.1% by weight of methacrolein. It was fed to a packed column for distillation.

The overhead product contained methacrolein, small amounts of low-boilers such as acetaldehyde, acetone and acrolein, and water. After cooling, the overhead product separated into two phases of which the excess phase was composed of about 92% by weight methacrolein.

We claim:

1. A process for removing methacrolein from a gaseous mixture comprising contacting said mixture with an aqueous solution containing methacrylic acid, and absorbing methacrolein into said solution, the content of methacrylic acid in the aqueous solution being from 60 to 90% by weight.

2. A process as claimed in Claim 1 wherein the absorption is carried out at from 5° to 50° C.

3. A process as claimed in Claim 1 wherein the methacrolein-containing mixture being contacted is obtained from the catalytic gas-phase oxidation of a 4 carbon organic compound to methacrolein and/or methacrylic acid.

* * * * *